United States Patent
Dykstra et al.

[19]

[11] Patent Number: 5,876,366

[45] Date of Patent: Mar. 2, 1999

[54] KIDNEY DIALYSIS METHOD AND DEVICE

[76] Inventors: Todd M. Dykstra, P.O. Box 1856, Salt Lake City, Utah 84110; Mary K. Towns, 2007 Stratford Dr., Salt Lake City, Utah 84109

[21] Appl. No.: 684,821

[22] Filed: Jul. 22, 1996

[51] Int. Cl.⁶ .................................................. A61M 37/00
[52] U.S. Cl. ........................................ 604/4; 128/DIG. 6
[58] Field of Search ................ 604/4–6, 28, 29, 604/48, 49, 86, 192, 174; 210/645, 646; 128/DIG. 26

[56] References Cited

U.S. PATENT DOCUMENTS

| | | | |
|---|---|---|---|
| 4,878,897 | 11/1989 | Katzin | 604/86 |
| 5,069,662 | 12/1991 | Bodden | 604/5 |
| 5,286,388 | 2/1994 | Ingram | 604/4 |
| 5,399,352 | 3/1995 | Hanson | 424/423 |
| 5,411,479 | 5/1995 | Bodden | 604/4 |
| 5,520,641 | 5/1996 | Behnke et al. | 604/86 |
| 5,622,626 | 4/1997 | Matkovich et al. | 604/4 |

*Primary Examiner*—John G. Weiss
*Assistant Examiner*—Ki Yong O
*Attorney, Agent, or Firm*—Mallinckrodt & Mallinckrodt; Philip A. Mallinckrodt

[57] ABSTRACT

A method of kidney dialysis by operation of a kidney dialysis machine includes use of unique AVF or a AVG sets or needle-like venous catheter whose blood-flow tubes are equipped with respective injection/administration port structures or fittings for the introduction of required or desired drugs or other additives into the body of a patient through an A-V access fistula or graft during operation of the machine or following disconnection from the machine while still emplaced in the body of a patient.

8 Claims, 2 Drawing Sheets

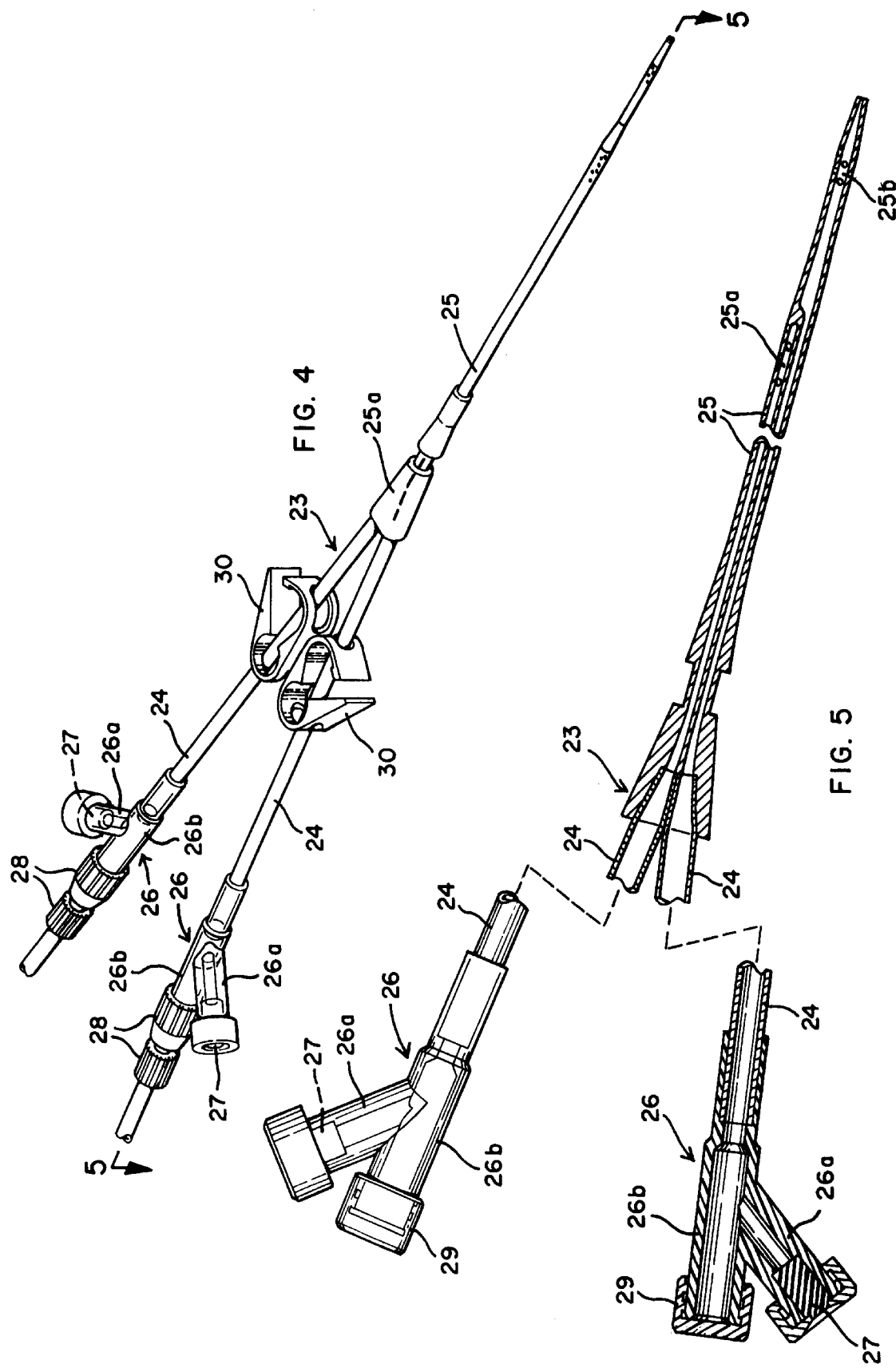

KIDNEY DIALYSIS METHOD AND DEVICE

BACKGROUND OF THE INVENTION

1. Field

The invention is in the field of kidney dialysis procedures and includes both method and devices.

2. State of the Art

The above-indicated field in the medical treatment of patients suffering from kidney problems has existed for many years. It is standard practice to use a dialysis machine equipped with a blood pump and carrying a so-called "extracorporeal blood circuit" for passing arterial blood drawn from the body of a patient through the dialysis unit and for returning the blood as dialyzed back to the venous system of the patient body of the patient. Both the drawing of the arterial blood and the insertion of the dialyzed blood into the venous system of the body may be accomplished by the use of tubular, dialysis access devices separate from the extracorporeal blood circuit.

One type of separate access device, often referred to as an A-V hemodialysis device, is known in the art as an AVF or an AVG dialysis set. Such a set is equipped with a special, large bore, dialysis needle for insertion into a specially provided artery/vein fistula (AVF) or artery/vein graft (AVG) of the patient's body and with a single, relatively short, blood-flow tube, to one end of which the dialysis needle is attached. The opposite end of this blood-flow tube is adapted for attachment to an open end of the extracorporeal blood circuit tubing of the dialysis machine. Thus, such an access device is normally used for temporary vascular access to the arterial system of a dialysis patient leading from the heart and for temporary vascular access to the venous system of the patient leading to the heart.

An A-V fistula is a patient's specially joined artery and vein into which special, large bone dialysis needles are inserted. An A-V graft joins an artery and vein of the patient by means of a short, interconnecting, blood-flow tube. Either of these special vascular access provisions may be made in the patient's body prior to the dialysis regimen, depending on circumstances.

The blood-flow tube of the AVF or AVG hemodialysis set is relatively short, about one foot in length, compared to the length of the extracorporeal blood circuit tubing, which is several feet in length. The extracorporeal tubing of the typical dialysis machine is equipped with flow shut-off clamps and so-called injection/administration port structures. These are usually positioned in respective, opposite end portions of the extracorporeal blood circuit tubing at the arterial and the venous sides, respectively, of the machine. Typically, utilitarian units additional to the dialysis unit, such as a venous drip chamber, a heparin infusion line, a connection for an IV saline solution bag, and arterial and venous pressure monitors, are provided in the extracorporeal blood circuit tubing of the machine.

The hemodialysis access devices are normally removed when the dialysis has been completed for the particular appointed treatment and after blood specimens have been withdrawn and any necessary or desirable drugs or other additions have been introduced into the patient's body through the injection/administration ports in the extracorporeal tubing of the dialysis machine. This has been routine procedure for the many years we have worked as a dialysis technician and a supervisory nurse, respectively, in kidney dialysis clinics..

It often happens, however, that introduction of the necessary and very expensive drugs is not effective for one reason or another, e.g. because of the overall length of blood-flow tubing leading from the dialysis unit to the patient and the tendency for drugs to be dissipated in the long travel through such tubing considering the usual placement of the injection/administration ports in the extracorporeal blood circuit of the machine. In such instances, we have attached a syringe to the inflow end of the blood-flow tube of the AVF or AVG hemodialysis set that has been removed from the machine but that is still emplaced in the body of the patient and have added a necessary or desired drug to the saline solution for introduction into the patient. Others in the field concerned may possibly have done and are continuing to do the same, but this is unsatisfactory because the introduction of different drugs at different times means that the syringe has to be repeatedly removed, emptied, sterilized, refilled with fresh saline solution and a different drug, and reattached. This necessitates repeated sterilizations of components or the use of several syringes that have been pre-prepared with respective quantities of saline solution and with respective drugs that must be independently introduced into the patient. This is also unsatisfactory because it allows the possible introduction of airborne contaminants into the patient or into blood from the patient, thereby contaminating the area.

Similar difficulties have existed with a different type of access device used in kidney dialysis and known as a "subclavian catheter" or a "central venous catheter", i.e., a "CVC". Such device is specially made for hemodialysis use by being provided with an elongate, dual lumen, needle-like, catheter dialysis portion for emplacement in the patient after a usual puncturing needle has prepared the way for such an emplacement in a subclavian vein or in a central vein of the body of a patient following penetration of the vein by such usual puncturing needle. Such a dialysis catheter has, as a patient access dialysis set, two relatively short tubes leading to the dual lumens, respectively, of the needle-like dialysis catheter portion.

SUMMARY OF THE INVENTION

In accordance with the invention, we now utilize an A-V hemodialysis access device, e.g. an AVF or AVG hemodialysis set or a subclavian or CVC needle-like dialysis catheter, having a simple, relatively short, blood-flow tube portion or a pair of same, respectively, in which is or are incorporated injection/administration port or ports. This enables such access device to continue to serve as does the extracorporeal blood circuit of the dialysis machine, but now independently of such machine, during a desired length of time in which the access device remains emplaced in the body of the patient.

The invention includes a patient access AVF or AVG hemodialysis set or a set in the form of a needle-like dialysis catheter having injection/administration port structure or port structures therein, whether as a commercial product for attachment to an open end of the extracorporeal blood circuit tubing of a dialysis machine and for implantation in a dialysis patient or whether formed by attaching an injection/administration port fitting to the free end of an already implanted hemodialysis set or dialysis catheter of usual type in order to practice the method of the invention. In the latter instance, sale of an injection/administration port fitting with intent that it be installed as here indicated would be regarded as constituting contributory infringement.

Although the change in position of the injection/administration port structure for a side of the machine as normally provided in the extracorporeal blood circuit tubing, or the addition thereto, is indeed a very simple one, it provides advantages not hitherto envisioned. Thus, an AVF or AVG hemodialysis set can be left connected to the fistula or graft in the patient's body after disconnection of the access device from the extracorporeal blood circuit of the dialysis machine and used repeatedly to introduce replacement or additional drugs into the patient, without significant loss of such drugs or danger of contamination by repeated handling as otherwise required. Moreover, neither these dialysis access sets nor the subclavian catheter type of dialysis access device need be connected to the extracorporeal blood circuit tubing of a dialysis machine every time samples of blood are to be taken or a drug or other additive is to be introduced into the patient's body.

We have found that the contribution of this invention to the hemodialysis art is of tremendous importance. Even though dialysis has been very widely used since Medicare funding for it was approved in 1972, the benefits to be achieved have apparently not been conceived of heretofore, nor has the simple way of achieving such benefits by the simple change in the A-V access device taught herein.

Thus, the present invention allows medication to be given almost directly into the patient's bloodstream, instead of through an unduly long, tubular portion of the extracorporeal blood circuit of a dialysis machine. Many drugs adhere to dialysis circuit components and never get into the patient's body, or those amounts that do arrive constitute ineffective doses, particularly antibiotics and the costly hormone erythropoietin, both of which are commonly given at the end of a dialysis treatment. Adequate drug levels of such medications are critical in the handling of life-threatening infections and of anemia often found in dialysis patients.

The invention also allows blood samples to be taken substantially directly from the patient's body instead of from the extracorporeal circuit. This enables far more accurate blood laboratory values to be obtained, especially for the common studies which determine recirculation or the adequacy of treatment.

Moreover, there are advantages related to convenience and patient/staff safety. In most emergency situations, dialysis treatment is immediately terminated, making the extracorporeal blood circuit useless in the administration of emergency drugs. In such situations, the hemodialysis access device must be separated from the circuit and attached to an infusion device such as a syringe before treatment can begin, costing valuable time and risking accidental needle discontinuation, blood loss, or the introduction of air or airborne pathogens into the patient. The ability to give drugs substantially directly into the patient's bloodstream following disconnection of the patient from the dialysis machine can literally save lives by enabling immediate use of emergency drugs. Beyond this, there are daily uses for a port in the dialysis access device, which enables the introduction of multiple medications, flushing liquid, and intravenous fluids without separation of the dialysis access device from the extracorporeal blood circuit tubing of the machine. Any time a system is opened, there is a risk of exposure to air or airborne pathogens into the patient, or the risk of blood exposure to staff, both of which situations are to be avoided whenever possible.

Further advantages result from the invention. In the subclavian and CVC dialysis catheter devices, unlike the usual dialysis needles which are typically inserted before dialysis and removed from the patient at the end of each treatment, such a catheter access device remains in the patient for an indeterminate amount of time and therefore requires a minimum three minute disinfection period at any connection site before the device can be safely opened and connected to the extracorporeal blood circuit. This is also true whenever the circuit is separated from the patient at the end of dialysis or whenever the system is opened. This process is not only inconvenient in the common practice of drawing blood from a patient or giving the patient medications, it can be deadly in an emergency. A staff member is then faced with the untenable choice of either risking a deadly infection in an already chronically ill patient or delaying the medication until the disinfection is complete. The added injection/administration port between the subclavian needle-like catheter portion of the device and its connection with the dialysis circuit tubing solves this problem as it does in the AVF and AVG sets. The catheter device is large bore for dialysis purposes and is inserted in the patient after central venous penetration by a usual penetrating needle.

The invention also eliminates a problem encountered with most methods of dialysis retransfusion, i.e., the return of the patient's blood at the end of dialysis. Most methods now used require opening the extracorporeal blood circuit prior to the retransfusion of blood. Many times, a patient's blood pressure is low at the end of dialysis, requiring the rapid transfusion of blood in order to prevent serious complications, such as seizures, vomiting, or loss of consciousness. If the dialysis access device must first be disconnected from the blood circuit of the machine (and disinfected as for the subclavian catheter), valuable time is lost and there is added risk of accidental needle discontinuance or introduction of air or airborne pathogens into the patient. With the invention, saline solution can be rapidly and safely attached to the arterial injection port and immediate, risk-free retransfusion accomplished without opening the circuit of the machine. Additionally, the invention is invaluable in instances of complications caused by venous needle loss or infiltration, which requires retransfusion through the arterial needle. The injection port of the dialysis access device can be used in this case without opening the system.

THE DRAWINGS

The best mode presently contemplated for carrying out the invention in actual practice is shown in the accompanying drawings in which:

FIG. 1 is a perspective view of a kidney dialysis system of the invention looking toward a typical dialysis machine thereof having the usual extracorporeal blood circuit tubing connected to an A-V fistula or to an A-V graph in the arm of a patient by inflow and outflow AVF or AVG hemodialysis sets, each set being equipped with a fitting that provides for an injection/administration port and thus constitutes a device of the invention;

FIG. 2, a perspective view of one of the novel hemodialysis sets of FIG. 1 drawn to a considerably larger scale and having a portion of its length broken out for convenience of illustration;

FIG. 3, a vertical, longitudinal, axial partial section through the relatively short, blood-flow tubing of the separate access device of FIG. 2, as taken on the line 3—3 of FIG. 2;

FIG. 4, a view corresponding to that of FIG. 2, but showing a subclavian or CVC catheter type of dialysis access device of the invention as connected to the open opposite ends, respectively, of the extracorporeal blood circuit tubing of the dialysis machine; and FIG. 5, a view corresponding to that of FIG. 3, but of the entire catheter access device of FIG. 4, as taken on the line 5—5 of FIG. 4 with intermediate portions of the tubing and of the needle-like catheter broken out for convenience of illustration.

DETAILED DESCRIPTION OF ILLUSTRATED EMBODIMENTS

Figure 1:
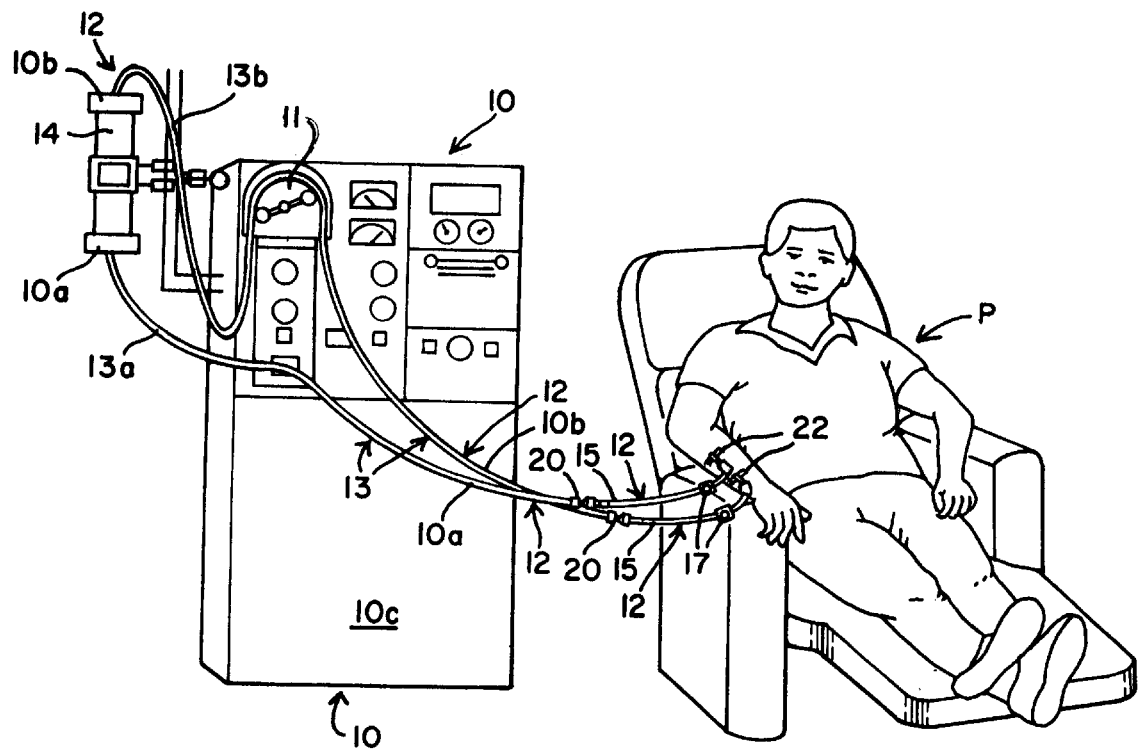

The method of the invention utilizes a largely conventional type of kidney dialysis system, such as that illustrated in FIG. 1, except for novel, separate, A-V hemodialysis access devices that are, as in the prior art, removably attached, respectively, to open end of the extracorporeal blood circuit tubing of a typical dialysis machine 10 having a conventional roller type blood pump 11 and a conventional, disposable and replaceable, elongate, tubular, extracorporeal blood circuit 12. Such circuit 12 comprises extracorporeal circuit tubing 13 having a portion leading from the blood-intake side 10a of the machine to the inlet of a usual dialysis unit 14, and having a portion leading from the outlet of such dialysis unit 14 to and through the pump 11 and on to the patient P from the delivery side 10b of the machine.

As previously indicated, the extracorporeal blood circuit tubing 13 is customarily provided as a disposable, single use part of the machine. Clamps (not shown) for the control of blood-flow and injection/administration ports (not shown) are normally provided in the intake and delivery portions 13a and 13b, respectively, of the circuit tubing 13 for taking blood samples from, and for introducing required or desired drugs and other additives into, the blood flowing through such circuit tubing 13 of the machine. Normally, other items not shown nor described herein, but well known to the art as part of the extracorporeal blood circuit of a dialysis machine, are included in the extracorporeal blood circuit 12 as previously mentioned.

In accordance with the present invention, such injection/administration ports as are conventionally provided in the circuit tubing 13 are unnecessary and may be eliminated from such circuit tubing, which tubing is usually removably hung on the machine's front wall 10c in full view of the operator as shown in FIG. 1.

The circuit tubing 13 terminates in free ends, respectively, at the intake and delivery sides 10a and 10b, respectively, of the machine and have separate, patient-access devices (see 15, FIGS. 1 and 2) of the invention removably attached thereto.

Patient-access devices as previously made and used are not equipped with an injection/administration port structures or fitting, but are entirely dependent for injection/administration purposes upon such a port or ports as provided in the extracorporeal circuit tubing of the prior art dialysis machine itself. So far as we are aware, there has not previously been any dialysis patient-access device separate from and independent of the dialysis machine that is equipped with an injection/administration port as is an access device 15 of the present invention, nor has there been any suggestion that the advantages taught herein could be achieved and that pre-existing problems could be overcome by the provision of injection/administration ports in the respective separate and independent patient-access devices that have heretofore been made and used.

Figure 2:
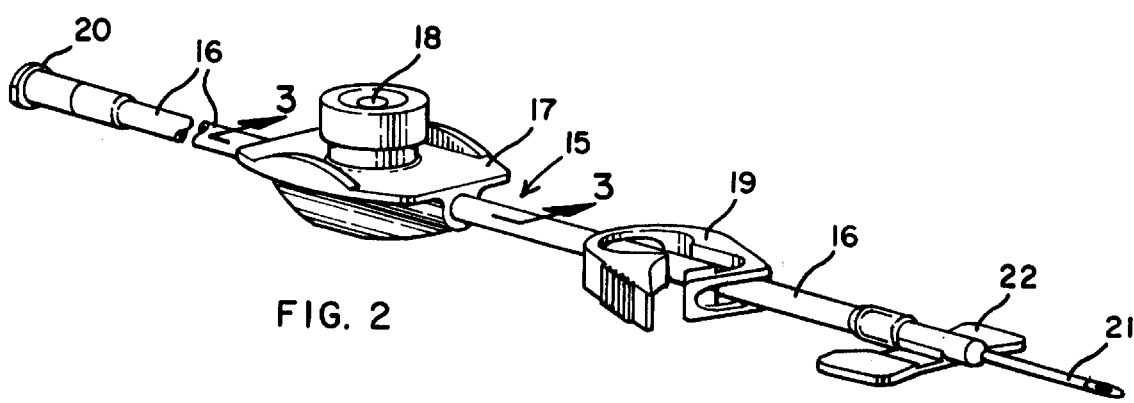
Figure 3:
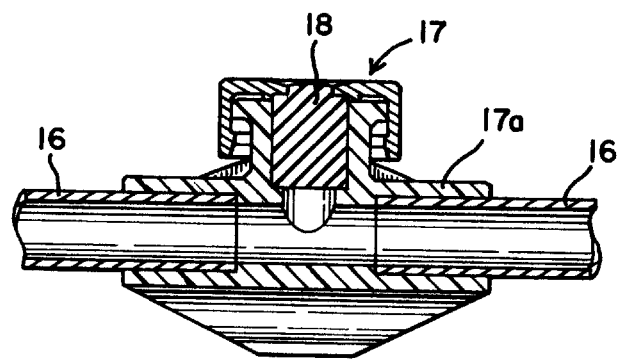

Thus, as indicated in FIGS. 1 and 2, patient-access devices 15, 15 of the invention are respective AVF or AVG hemodialysis sets, each having blood-flow tubing 16, FIGS. 2 and 3, that is short in overall length compared to the overall length of the tubing 13 of the usual extracorporeal blood circuit 12, and that is equipped with an injection/administration port structure or fitting 17 and a needle or a so-called needleless (a needle formed of plastic) penetration fitting. As here shown, such port fitting 17 is a usual, advanced type of port fitting having an inverted T form of blood flow connector 17a for insertion of the cross portion thereof between free ends of a transverse cut in the tubing 16 and with a soft rubber stopper 18 in the usually upstanding stem of the T. Such fitting is open at the top for insertion through stopper 18 of a liquid-flow, penetration needle or a plastic needle of a needleless injection system. A usual type of clamp 19 is also provided in the tubing 16, and a free end of such tube is adapted for easily removable connection with the free end of circuit tubing 13 at either the blood inflow side 10a or the blood delivery side 10b of the dialysis machine 10, or to a syringe filled with saline solution, as by some type of the usual Luer connector 20. The opposite end of such short blood flow tubing 16 has a usual, special, large bore, dialysis needle 21 attached thereto for puncturing, and for emplacement in, the special fistula or graft (not shown) of the patient. The hub of needle 21 desirably has a transverse, graspable, and upwardly bendable, holding element 22 rotatably or solidly affixed thereto for use in advancing the needle into the fistula or graft of the patient's body.

A different type of patient-access device 23 is shown in the embodiment of FIGS. 4 and 5, wherein, in place of the single tube 16 and of the usual, special, large bore, puncturing type of dialysis needle 21, it has a pair of tubes 24, 24 branching from a single hub portion 25a of a non-puncturing, plastic, insert needle 25 in the form of an elongate, dual lumen, needle-like catheter for emplacement in a vein of the patient for long term use. Such patient-access device 23 is the subclavian catheter or CVC previously mentioned as adapted for dialysis use and, as illustrated in FIGS. 4 and 5, the needle or needle-like dialysis catheter portion 25 is attached to the otherwise free ends of the pair of tubes 24. Such tubes 24, 24 have corresponding free ends to which are attached respective port fittings 26, 26 each similar to the injection/administration port structure or fitting 17 in that it has a soft rubber stopper, here indicated 27, as a puncturable part in a branched portion 26a of the sealing port fitting 26, which is Y-formed with a stem portion 26b adapted to connect with a free end of the extracorporeal blood circuit tubing 13 of the dialysis machine 10 as by a Luer type fitting 28, FIG. 4, and to be closed by a removable cap 29, FIG. 5, when disconnected from the machine. Also, each of these port fittings is normally accompanied by a flow shut-off clamp 30. One of the tubes 24 connects with one lumen 25a of the dual lumens of dialysis catheter 25, while the other tube 24 connects with the other lumen 25b of such dual lumens.

It is convenient to mount such port fittings 26 at the dialysis-machine-connecting ends of the patient-access devices 23, but here, as in the other dialysis access devices of the invention, they may be positioned at any convenient location along the tubular length of such access device, it being preferable to have them about three inches back of the hub of the needle.

As previously indicated, the invention contemplates that the usual type of hemodialysis access device, whether an AVF or AVG dialysis set or a needle-like dialysis catheter, that is already implanted in a patient, can be converted to a device of the invention without removal from the patient's body by connecting an injection/administration fitting, such as a fitting 17, FIG. 3 by means of a Luer type connector, such as the connector 20, FIG. 1, or the connector 28, FIG. 4 to the free end of the tubular portion of an emplaced, usual dialysis set, or injection/administration structures or fittings, such as 26, FIG. 5, to the free end of each of the dual tubes 24 of the needle-like dialysis catheter.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A kidney dialysis method, comprising utilizing a dialysis machine having extracorporeal blood circuit tubing adapted for blood flow connection with blood flow tubing of separate, patient access dialysis sets for the passage of blood from and to a dialysis patient relative to a dialysis unit within said extracorporeal blood circuit tubing of the machine; connecting end portions of the blood flow tubing of such separate patient access dialysis sets in blood flow relationship with said extracorporeal blood circuit tubing by connector fittings attached to the blood flow tubing of said separate patient dialysis sets, respectively, which sets are equipped with dialysis needle means and injection/administration port structures, the blood flow tubing of said patient dialysis sets being short compared with the length of said extracorporeal blood circuit tubing of said dialysis machine; passing blood withdrawn from the dialysis patient through the dialysis unit of said machine; reinserting the withdrawn blood as dialyzed back into the patient's body; and utilizing the injection/administration port structures of the patient access sets for injecting drugs or other additives into the patient or for withdrawing samples of the patient's blood.

2. A method according to claim 1, wherein the injection/administration port structures of the patient access dialysis sets have ports, respectively, closed by puncturable sealing closures.

3. A method according to claim 1, wherein the dialysis needle means of the patient access dialysis sets are large bore dialysis needles.

4. A method according to claim 1, wherein the dialysis needle means of the patient access dialysis sets include a needle-like catheter.

5. A kidney dialysis patient access set for attachment to the extracorporeal blood circuit tubing of a dialysis machine, comprising blood flow tubing short compared to the length of the extracorporeal blood circuit tubing of a dialysis machine to which said patient access set is to be attached, one end portion of said short blood flow tubing being provided with connector fitting or fittings for connection to the extracorporeal blood circuit tubing of the dialysis machine; dialysis needle means connected to the opposite end of said short blood flow tubing of the patient access set for insertion into the body of a dialysis patient; and injection/administration port structure connected into said short blood flow tubing of the patient access set and adapted for use in either removing blood specimens from the body of the dialysis patient or in introducing drugs or other additives to the body of the dialysis patient.

6. A kidney dialysis patient access set according to claim 5, wherein the injection/administration port structure has a needle puncturable, sealing closure.

7. A kidney dialysis patient access set according to claim 5, wherein the dialysis needle means is a large bore dialysis needle.

8. A kidney dialysis patient access set according to claim 5, wherein the dialysis needle means is a needle-like, venous catheter.

* * * * *

UNITED STATES PATENT AND TRADEMARK OFFICE
CERTIFICATE OF CORRECTION

PATENT NO. : 5,876,366
DATED : March 2, 1999
INVENTOR(S) : Todd M. Dykstra and Mary K. Towns It is certified that error appears in the above-identified patent and that said Letters Patent is hereby corrected as shown below:

Column 1, line 36, "bone" should be changed to --bore--.

Signed and Sealed this

Twenty-fourth Day of August, 1999

Attest:

Q. TODD DICKINSON

*Attesting Officer*      *Acting Commissioner of Patents and Trademarks*